United States Patent [19]

Sikes et al.

[11] 3,940,943
[45] Mar. 2, 1976

[54] MULTISTAGE FREEZING SYSTEM FOR PRESERVATION OF BIOLOGICAL MATERIALS

[75] Inventors: John D. Sikes; Charles P. Merilan, both of Columbia, Mo.

[73] Assignee: The Curators of the University of Missouri, Columbia, Mo.

[22] Filed: Jan. 22, 1975

[21] Appl. No.: 543,029

[52] U.S. Cl. .................... 62/64; 62/65; 128/1 R; 195/1.8; 424/180
[51] Int. Cl.² ................................ F25D 17/02
[58] Field of Search .......... 62/62, 64.5, 78; 195/1.7, 195/1.8; 128/1 R; 424/180

[56] References Cited
UNITED STATES PATENTS

| | | | |
|---|---|---|---|
| 3,303,662 | 2/1967 | Moline et al. | 62/62 |
| 3,677,024 | 7/1972 | Segall | 195/1.8 |
| 3,683,635 | 8/1972 | Campanelli | 62/64 |
| 3,729,947 | 5/1973 | Higuchi | 62/62 |
| 3,758,382 | 9/1973 | Knorpp | 424/180 |

Primary Examiner—William E. Wayner
Assistant Examiner—Ronald C. Capossela
Attorney, Agent, or Firm—Ray E. Snyder

[57] ABSTRACT

A carefully controlled, multistage freezing and thawing process for the preservation of animal semen, blood, and other biological materials. A variety of diluting substances can be utilized to effectively modify the cell membrane's permeability to water and to initiate and/or alter the process of crystallization to minimize undesirable physio-chemical effects.

A sample of semen is diluted with a suitable cryoprotective agent to achieve a final pH of 6.0 to 6.3 at +5°C. The sample is collected at body temperature and cooled slowly to +5°C, held at this temperature for 30 minutes or longer, followed by a rapid decrease in temperature to a nominal −4°C, or a temperature slightly below the freezing point of the diluent. The sample is held at this temperature for a period of 1 to 8 minutes to allow adjustment and stabilization of the temperature induced changes in pH and associated alterations in membrane permeability and osmotic pressure. The sample is then cooled rapidly after stabilization down to a nominal −100°C at a nominal rate of 20°C/minute. The sample is then immersed into liquid nitrogen for final cooling and storage.

Rapid thawing is also an essential step in the total process to enhance cell survival. Semen or other biological materials in ampules may be thawed by immersing the ampules in +45°C water for 15 to 30 seconds while semen packaged in straws will thaw within 5 to 7 seconds in +45°C water.

2 Claims, 1 Drawing Figure

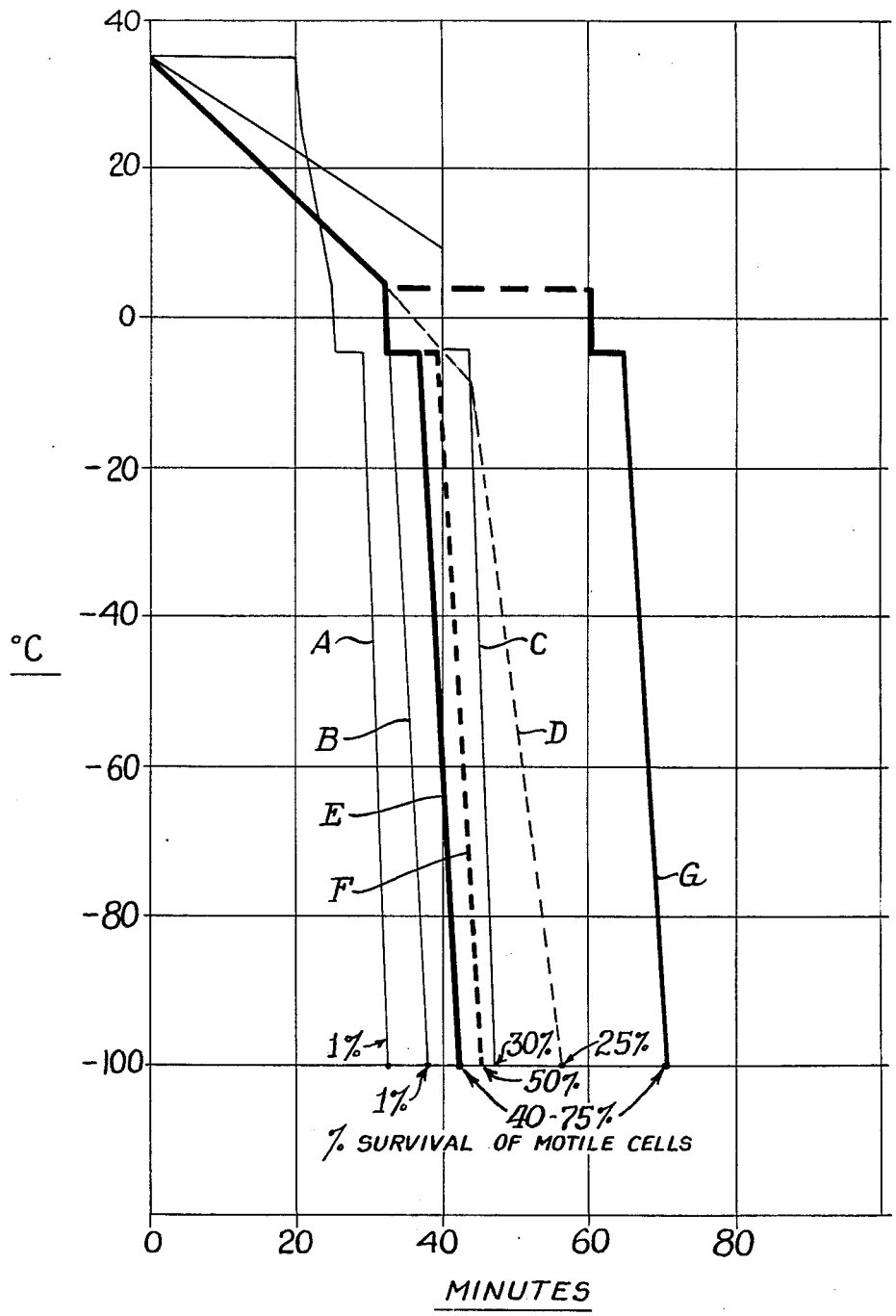

MULTISTAGE FREEZING SYSTEM FOR PRESERVATION OF BIOLOGICAL MATERIALS

BACKGROUND OF THE INVENTION

1. Field of the Invention

This invention relates generally to the field of cold storage preservation of living cells, and more particularly to the process for preparing such cells for deep-freezing preservation, and the subsequent process of thawing to revive such cells.

2. Description of the Prior Art

The use of cold temperatures for the preservation of biological materials is well known. The field of artificial insemination of animals is dependent upon the ability to freeze a specimen of animal semen for storage and shipment, to thaw it for use, and to have a sufficient number of sperm cells survive to be effective. The freezing and thawing processes are a severe shock to any living cell and can cause serious chemical and structural phase changes in the cell.

Glycerol was found, in 1949, to provide a protective effect for bovine semen against the shock of deep freezing — down to liquid nitrogen temperatures. This discovery was extended to the preservation of a variety of biological materials, including whole blood. The glycerol normally is used in a concentration of 5% to 10% of the semen or other biological material.

Unfortunately, glycerol has been found to be toxic at the concentrations in use, and particularly so when the specimen is exposed to ambient temperatures for extended periods of time. This adverse reaction has precluded its use with some biological materials. For some materials, including whole blood, a low temperature dialysis procedure is required for removal of the glycerol after the material is thawed and prior to its use.

A number of cryoprotective diluents, other than glycerol, have been tried and reported in the patent and technical literature. These include: dimethylsulfoxide, high molecular weight sugars (e.g. lactose, raffinose, etc.) and polymeric hydrocarbons such as polyvinylprolidone. Organic buffering afents such as TRIS (trishydroxymethylamino methane) and TES N tris(hydroxymethyl) methyl-2-aminoethane sulfonic acid have also been incorporated in some cryoprotective diluents. Examples of other diluters are taught in the patents to Smith et al., U.S. Pat. No. 3,185,623; and to Folkers et al. U.S. Pat. No. 3,306,818. However, glycerol has remained the cryoprotective diluent of choice for commercial processing of "frozen semen."

The freezing process per se, and particularly the rate of cooling for preparing "frozen semen," has also been a subject of extensive study. The general consensus from these studies recommends, for 1 ml. ampules of semen, a slow cooling rate (1°C per minute) from approximately +4°C to −15°C followed by a nominal 3-fold increase in the cooling rate. For "ampule freezing," this continues to be the generally used procedure.

An alternative "vapor freezing" technique, particularly for freezing semen in glass or plastic straws has also been employed. This involves suspending the straws filled with semen and diluent above the surface of a liquid nitrogen bath. After the samples are frozen, they are then immersed in the liquid nitrogen for storage. This technique is still widely used for both ampules and straws.

A third technique involves "pellet freezing" of semen and diluent. A droplet of approximately 0.07 ml. diluted semen is placed directly upon the surface of "dry ice" and allowed to remain until frozen. The pellet is subsequently transferred into liquid nitrogen for storage.

All of the above described methods have been predicated upon empirically derived slow cooling rates, usually involving the classical "supercooling temperature curve." This classical curve denotes crystallization from a supercooled state. The "pellet freezing" technique may appear to be an exception, but, in fact, is not. The sublimation of $CO_2$ increases in the region immediately below the droplet of semen, thus forming essentially an insulating blanket of gas which effectively slows the cooling rate. As the temperature of the semen droplet decreases, the $CO_2$ evolution slows, and the cooling rate of the droplet is then increased. As a consequence of these interactions between the semen droplet and the "dry ice" surface, the relative cooling rate of the sample is still that which is generally characterized as slow freezing.

The rate of thawing of semen samples has also received some study, but relatively little in comparison to the freezing process. Generally, glycerol protected samples thawed at body temperature or in ice water have given acceptable fertility rates.

SUMMARY OF THE INVENTION

It is an object to provide an improved integrated systems process for the cryogenic preservation and storage and subsequent use of sensitive biological materials.

It is a more particular object to provide a carefully controlled, multistage freezing and thawing process for the preservation of animal semen, blood and other biological materials.

A variety of diluent materials can be used as cryoprotective agents in conjunction with the freezing process. Protective agents of choice are the disaccarides including lactose, maltose and raffinose.

It is another object to provide an improved and effective freezing process that does not require the use of glycerol as a diluent. In some applications, it may be possible to use glycerol in substantially reduced quantities, i.e. below toxic levels.

The diluted semen or other biological material is carried through a carefully controlled freezing curve that is staged at critical times so as to minimize the deleterious effects of temperature and related chemical and structural phase changes that take place during the freezing stage.

It is a supplemental object to include an improved thawing process in conjunction with the improved freezing process so as to further increase the survival rate of living cells.

DETAILED DESCRIPTION OF THE INVENTION

The preferred method for carrying out the improved process of the present invention may best be understood by following these numbered steps:

1. Preparation of cryoprotective agent.

A variety of agents can be utilized so long as they are effective to modify the cell membrane's permeability to water and to initiate and/or alter the process of crystallization of cellular fluids. For bovine semen preservation, an example of a suitable agent may be a disaccaride concentration in the range of 0.2 to 0.25 molar for the total diluent:semen mixture. A typical formulation could be 3 parts of diluent (11% lactose and 7.5% to 25% egg yolk made to volume with distilled water) plus 1 part semen.

2. Dilution of semen.

The prepared cryoprotective agent should be added to the semen immediately after collection, while the semen is warm. The dilution should be made in such a manner as to achieve a final pH of 6.0 to 6.3 at +5°C. The egg yolk concentration and the hydrolysis of the disaccharide, as affected by heating, are variables which can be used do compensate for the pH and buffering capacity of the semen.

3. Packaging of diluted semen.

Any packaging of the diluted semen into ampules or straws, or other type containers should take place prior to cooling. At the latest, the semen should be packaged before the samples are cooled below +5°C.

4. Initial cooling of diluted semen.

After dilution and/or packaging, the semen should be cooled slowly to a nominal +5°C, or within the range of +3°C to +8°C. Preferably, the cooling rate should be less than 1 degree Centigrade per minute from body temperature down to the +5°C level. The time period during which the diluted semen is held at this temperature may be from 30 minutes to several hours and may be varied to help optimize the cooling and/or packaging procedure.

5. Initial freezing process.

This step which is an essential element of the invention involves a very rapid decrease in temperature from the nominal +5°C to a nominal −4°C. The latter temperature should be close to, but only slightly below, the freezing point of the diluent:semen mixture. A temperature more than a few degrees below this freezing point results in the death of the cells. The actual freezing temperature may vary with the mixture, but normally will lie in the range of −0.5°C to −6°C.

6. Maintenance of constant temperature.

The initial freezing temperature of a nominal −4°C should be maintained constant for a sufficient period of time to allow adjustment and stabilization of the temperature induced changes in pH and associated alterations in membrane permeability and osmotic pressure. The time required for this stabilization to take place may range from 1 to 6 minutes for semen packaged in straws, ampules, or sprayed in nebulized form onto cold packaging surfaces.

7. Second stage of the freezing process.

This stage of the freezing process involves rapid cooling of the frozen samples from the nominal −4°C down to a nominal −100°C. (For this prupose, a modified Linde Biological Freezer, No. BF-4-2 may be used). The optimum rate of cooling in this stage is largely dependent upon the type of packaging and sample volume. Typically, for nebulized, straw, and ampule packaged semen, the cooling rates should be approximately 30°C/min., 20°C/min., and 10°C/min., respectively. The temperature decreases must be sustained because warming fluctuations are detrimental to cell survival, even during the lower temperatures of this stage.

8. Third stage of the freezing process.

This stage involves the direct immersion of the samples from the second stage into liquid nitrogen for final cooling and storage.

9. Thawing of samples prior to use.

Rapid thawing of the frozen samples from liquid nitrogen temperatures to warm water temperatures is an important adjuct to the complete preservation system. The optimum temperature of thawing is related to volume of material involved. Typically, the samples should be thawed by immersion into +45°C water. Ampules should be immersed for 15 to 30 seconds, while semen packaged in straws will thaw within 5 to 7 seconds at this temperature.

BRIEF DESCRIPTION OF THE DRAWING

The FIGURE is a graph of a plurality of cooling curves showing the effect on sperm survival for various operative conditions.

DETAILED DESCRIPTION OF THE DRAWING

The graph of the FIGURE shows a plot of a plurality of experimentally obtained freezing curves and the survival rates realized by following the illustrated procedures. Survival rates were obtained by counting the number of progressively motile cells in a series of microscope fields and taking this as a percentage of the total number of cells in the respective fields. Samples were diluted to provide a total count of between 20 and 50 cells pef field. This graph illustrates the extreme criticallity of following the cooling procedure through the prescribed stages.

Curve A shows that the sample was maintained at an elevated temperature for a period of 20 minutes prior to cooling and was then cooled rapidly to −4°C, without significant pause at +5°C. This procedure realized less than 1% survival.

Curve B shows a sample that was cooled slowly to +5°C and then cooled rapidly to −100°C without pause at −4°C. This procedure also realized less than 1% survival.

Curve C shows the effect of a still slower rate of cooling, i.e. 40 minutes from 35°C to +10°C and then rapid cooling from +10°C to −4°C and held for 4 minutes at this temperature. The sample was then cooled rapidly to −100°C. This procedure yielded about a 30% survival rate.

Curve D shows a conventional cooling curve, i.e. slow cooling from +35°C to −8°C, and more rapid cooling from −8°C to −100°C. This conventional cooling rate in the range of −8°C to −100°C is slower than recommended by the process defined by the present invention. This conventional procedure yielded about a 25% survival.

Curve E is a plot of the cooling rate that begins to approach the procedure recommended by the present invention. The sample is cooled slowly to +5°C and rapidly to −4°C. The sample is held at this latter temperature for about 8 minutes and then cooled rapidly to −100°C. The measured survival rate was about 40%.

Curve F is similar to Curve E except that the sample was held at −4°C for an additional 2 minutes. This change in procedure yielded a 50% survival rate.

Curve G differs from Curve E only by virtue of a holding period of 30 minutes at +5°C. This was followed by a cooling rate equivalent to that of Curve E. The survival rate for this procedure was about 75%.

The empirically obtained curves above indicate there are two temperatures at which stabilization or equilibration must be allowed to take place. These temperatures are the nominal +5°C and the nominal −4°C. The time periods for which the samples can or should be held at these temperatures are available depending on interactions between particular samples and their cryoprotective agents. The holding times may also be limited by other physical-chemical changes that take place. For example, the age of the collected cells has been found to be one factor that effects holding times. Older cells appear to require less time to stabilize.

The length of the holding period at +5°C has been found to be less critical than at −4°C. The holding period at +5°C has not been found to affect the survival rate when extended from the indicated 30 minutes up to several hours. However, the 30 minute holding period appears to be near optimal.

The pause for a few minutes at −4°C is critical. The curves above show that no pause is very detrimental, i.e. only 1% survival, and extending the pause beyond the point of crystallization is also detrimental. The optimum holding time span appears to be 2 to 6 minutes.

The curves shown on the drawings are depicted as straight lines for the purposes of description of the steps taken and it is to be understood that the actual changes in temperature may be other than linear.

The survival rates were determined by direct microscopic observation of the semen samples before freezing, and following freezing and subsequent thawing. Relative counts were made of living vs. dead cells. In addition, video-tape recordings were made of the microscopic fields to record the relative motility of the sperm cells before freezing and following freezing and thawing.

It was found that the motility of the surviving cells after thawing was only slightly diminished from that of the unfrozen cells.

In addition, it was found that the motility of the live cells was significantly greater than that of cells frozen by conventional processes, when comparable video-recordings were made of the latter.

The combined advantages of increased suvival rates and sustained motility are readily projectible to increased fertility rates in inseminated cows, or alternatively, the same fertility rates with extended semen.

The invention taught herein is not to be considered as limited to the process described, except insofar as the claims may be so limited.

We claim:
1. A process for the cryo-preservation of living cells comprising the steps of:
    collecting a sample of living cells at ambient temperature;
    diluting the sample collected with a liquid cryo-protective agent;
    slowly cooling the mixture of cells and agent to a temperature in the range of about +3°C to +8°C;
    rapidly cooling the mixture to a temperature just below the freezing point of the mixture;
    holding the mixture at just below freezing for a short period of time sufficient to allow adjustment and stabilization of the temperature induced changes in pH and alterations in membrane permeability and osmotic pressure; and
    rapidly cooling the mixture to cryogenic storage temperature.

2. A process for the cryo-preservation of living cells comprising the steps of:
    collecting a sample of living cells at ambient temperature;
    diluting the sample collected with a liquid cryo-protective agent;
    slowly cooling the mixture of cells and agent to a temperature in the range of about +3°C to +8°C;
    holding the mixture within said temperature range for a period of from about 30 minutes to several hours;
    rapidly cooling the mixture to a temperature just below the freezing point of the mixture in the range of −0.5°C to −6°C;
    holding the mixture within said latter temperature range for a period of about 1 to 6 minutes; and
    rapidly cooling the mixture to cryogenic temperature.

* * * * *